US008845098B2

(12) United States Patent
Uchida (10) Patent No.: US 8,845,098 B2
(45) Date of Patent: Sep. 30, 2014

(54) OPTICAL COHERENCE TOMOGRAPHY APPARATUS, METHOD OF CONTROLLING OPTICAL COHERENCE TOMOGRAPHY APPARATUS, STORAGE MEDIUM, AND OPHTHALMIC SYSTEM

(75) Inventor: Hiroki Uchida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 30 days.

(21) Appl. No.: 13/427,378

(22) Filed: Mar. 22, 2012

(65) Prior Publication Data
US 2012/0249954 A1 Oct. 4, 2012

(30) Foreign Application Priority Data
Mar. 31, 2011 (JP) .................................. 2011-079802

(51) Int. Cl.
*A61B 3/10* (2006.01)
(52) U.S. Cl.
CPC ...................................... *A61B 3/102* (2013.01)
USPC ............................................ 351/208; 396/18
(58) Field of Classification Search
USPC ............. 351/205–221, 246; 396/18; 356/450, 356/477, 479, 496, 497
See application file for complete search history.

(56) References Cited

U.S. PATENT DOCUMENTS

| 7,370,967 | B2 * | 5/2008 | Tanifuji et al. | 351/206 |
| 7,604,351 | B2 | 10/2009 | Fukuma et al. | |
| 7,837,328 | B2 | 11/2010 | Fukuma et al. | |
| 2009/0244485 | A1 * | 10/2009 | Walsh et al. | 351/221 |
| 2011/0051088 | A1 * | 3/2011 | Shimizu et al. | 351/206 |
| 2011/0228222 | A1 * | 9/2011 | Kobayashi | 351/206 |

FOREIGN PATENT DOCUMENTS

| EP | 1 872 713 A1 | 1/2008 |
| JP | 2007-185244 A | 7/2007 |
| JP | 2008-5987 A | 1/2008 |
| JP | 2008-246158 A | 10/2008 |
| JP | 2009-279031 A | 12/2009 |
| JP | 2010-110391 A | 5/2010 |
| WO | 2009/141948 A1 | 11/2009 |

* cited by examiner

Primary Examiner — Darryl J Collins
Assistant Examiner — Gary O'Neill
(74) Attorney, Agent, or Firm — Fitzpatrick, Cella, Harper & Scinto (57) ABSTRACT

An optical coherence tomography apparatus includes: an acquisition unit configured to split light from a light source into measurement light and reference light, and acquire a tomogram of an eye to be examined based on interfering light obtained by interference between the reference light and return light from the eye; a positional relationship changing unit configured to change a positional relationship between the eye and an optical system including an optical path of the measurement light; and a control unit configured to control the changing unit based on a difference in slant information of the eye between two tomograms acquired by the acquisition unit.

32 Claims, 9 Drawing Sheets

OPTICAL COHERENCE TOMOGRAPHY APPARATUS, METHOD OF CONTROLLING OPTICAL COHERENCE TOMOGRAPHY APPARATUS, STORAGE MEDIUM, AND OPHTHALMIC SYSTEM

BACKGROUND OF THE INVENTION

1. Field of the Invention

The present invention relates to an optical coherence tomography apparatus, a method of controlling the optical coherence tomography apparatus, a storage medium, and an ophthalmic system.

2. Description of the Related Art

Currently, various types of ophthalmic apparatuses using optical apparatuses are used. For example, various types of apparatuses, such as an anterior ocular segment imaging apparatus, a fundus camera, and a scanning laser ophthalmoscope (SLO), are used as optical apparatuses for observing the eyes. Of these apparatuses, an optical coherence tomography apparatus based on optical coherence tomography (OCT) using multiwavelength interference is an apparatus capable of obtaining a tomogram of the eye to be examined with a high resolution. This apparatus will be referred to as an OCT apparatus hereinafter. The OCT apparatus has currently been becoming an indispensable apparatus as an ophthalmic apparatus for out-patient clinics dedicated to retinal diseases.

An OCT apparatus is an apparatus which irradiates a sample with measurement light, which is low-coherent light, and can measure backscattered light from the sample with high sensitivity by using a coherence system. The OCT apparatus can capture a tomogram of the retina of the eye to be examined with a high resolution, and hence is widely used for ophthalmic diagnosis and the like of the retinas. In addition, the OCT apparatus is widely used for progress observation to precisely check the patient's progress after an operation or to precisely check the advancement of eye disease.

In order to perform progress observation using such an OCT apparatus, it is necessary to compare tomograms of the same region in the eye to be examined in the X and Y directions. For example, Japanese Patent Laid-Open No. 2008-5987 discloses a technique of storing the scanning position of a tomogram captured in the past, and reproducing the scanning position in the X and Y directions at the next imaging time to perform imaging. This technique is configured to use, as information indicating a scanning position, driving information of a galvano mirror for scanning measurement light (for example, the reflection angle, operation pattern, and the like of the mirror) and reproduce the same driving information at the next imaging time.

Japanese Patent Laid-Open No. 2010-110391 discloses a technique of storing a scanning position at which a tomogram was captured in the past, in association with a fundus observation image at the time of tomography to compare tomograms of the same region of the eye to be examined in the X and Y directions. This technique is configured to compare a past fundus observation image with a current fundus observation image and correct the scanning position of a tomogram to be currently captured in the X and Y directions based on the positional shift amount between the tomograms.

In order to observe the progress of the eye to be examined using the OCT apparatus, it is important to not only image the same region in the X and Y directions but also to perform matching of the coherence gate (a position corresponding to a reference optical-path length in a measurement optical path), the slant, the brightness, and the like between tomograms to be compared. If, however, layer thicknesses are measured, for example, without achieving matching in the slant between tomograms to be compared, different distances are obtained with respect to the same layer because layer thicknesses are generally measured in the Z direction of tomograms. This poses a problem in terms of measurement accuracy. In addition, if layer detection is performed without achieving matching in brightness between tomograms, for example, a layer detected in a past tomogram may be not detected in a current tomogram. This poses a problem in terms of measurement accuracy.

SUMMARY OF THE INVENTION

The present invention has been made in consideration of the above problems, and provides an optical-coherence-tomography technique which can easily capture tomograms suitable for progress observation.

According to one aspect of the present invention, there is provided an optical coherence tomography apparatus comprising: an acquisition unit configured to split light from a light source into measurement light and reference light, irradiate an eye to be examined with the measurement light through a measurement-light optical path, guide the reference light to a reference-light optical path, and acquire a tomogram of the eye based on interfering light obtained by interference between the reference light and return light from the eye; a positional relationship changing unit configured to change a positional relationship between the eye and an optical system including an optical path of the measurement light; and a control unit configured to control the changing unit based on a difference in slant information of the eye between two tomograms acquired by the acquisition unit.

According to this present invention, it is possible to easily capture tomograms suitable for progress observation. For example, it is possible to achieve matching not only in position in the X and Y directions between tomograms to be compared, but also to achieve matching of the coherence gate (a position corresponding to a reference optical-path length in a measurement optical path), the slant, the brightness, and the like. This makes it possible to easily capture tomograms suitable for progress observation.

Further features of the present invention will become apparent from the following description of exemplary embodiments (with reference to the attached drawings).

DESCRIPTION OF THE EMBODIMENTS

Figure 1:
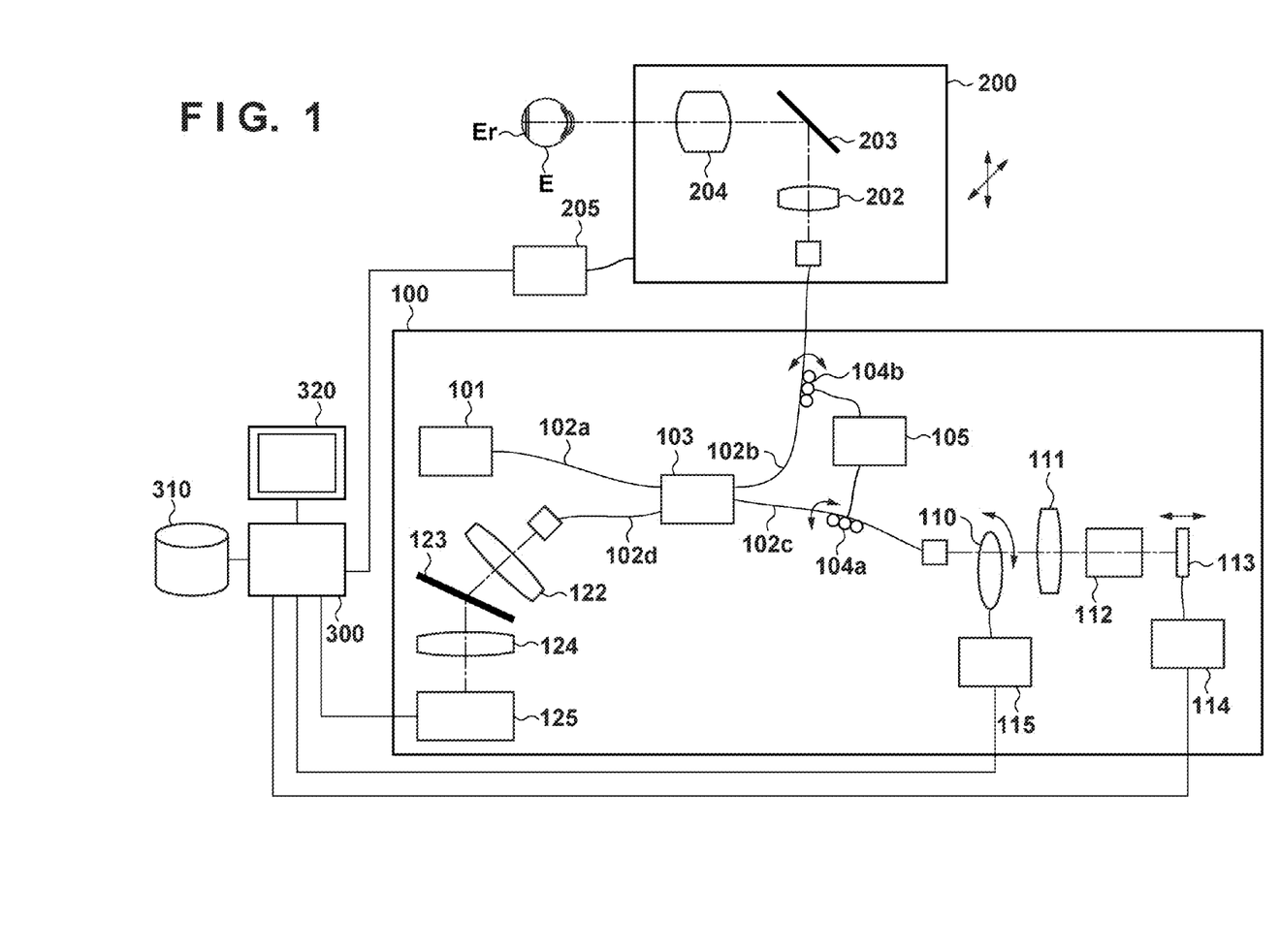
FIG. 1 is a view showing an example of the arrangement of an optical coherence tomography apparatus according to an embodiment of the present invention.

An optical coherence tomography apparatus according to this embodiment will be described with reference to FIG. 1. An optical base unit 100 will be described first. A light source 101 is a low-coherence light source which emits a near infrared ray. The light emitted from the light source 101 propagates through an optical fiber 102a. A light splitting unit 103 splits the light into measurement light and reference light. The measurement light split by the light splitting unit 103 enters an optical fiber 102b and is guided to an optical head unit 200.

Figure 9:
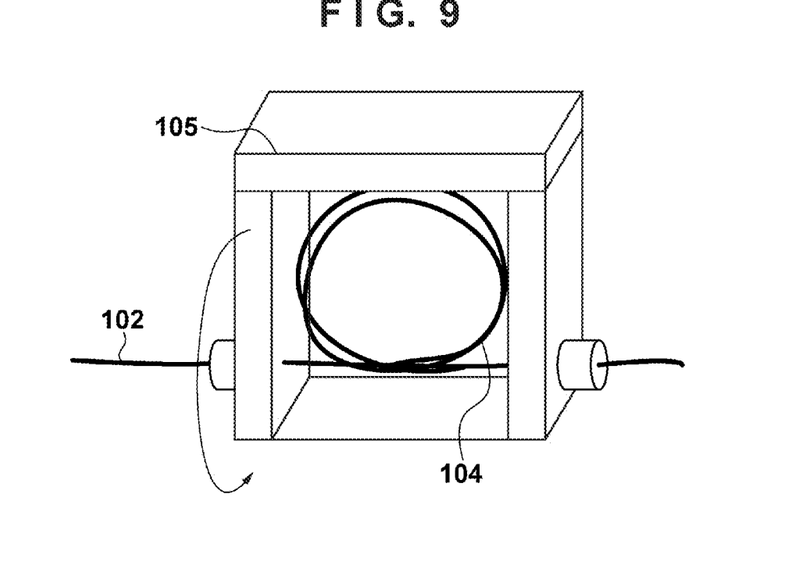
FIG. 9 is a perspective view for exemplarily explaining a polarization changing unit.

The reference light split by the light splitting unit 103 enters an optical fiber 102c and is guided to a reflecting mirror 113. The reference light which has entered the optical fiber 102c emerges from the fiber end through a fiber loop 104a for changing the polarization of the reference light. A polarization changing unit 105 is a control unit capable of driving the fiber loop 104a and a fiber loop 104b. As shown in FIG. 9, the polarization changing unit 105 twists an optical fiber 102 and controls the polarization of reference light by driving a fiber loop 104. Return light from the object to be examined (eye to be examined) irradiated with measurement light differs in polarization from reference light to cause a deterioration in the image quality of a tomogram. In order to solve this, it is preferable to match the polarization of return light with that of reference light. As a means for solving this, the fiber loop 104a may be automatically controlled based on the detection result obtained by a detection unit such as a line sensor 125. More specifically, the fiber loop 104a is controlled to increase the output of the line sensor 125. It is preferable to perform such an automatic control operation at a time after focus adjustment. This makes it possible to automatically perform not only focus adjustment, but also polarization adjustment. Note that the same control operation may be performed with respect to the fiber loop 104b (to be described later).

Figure 10:
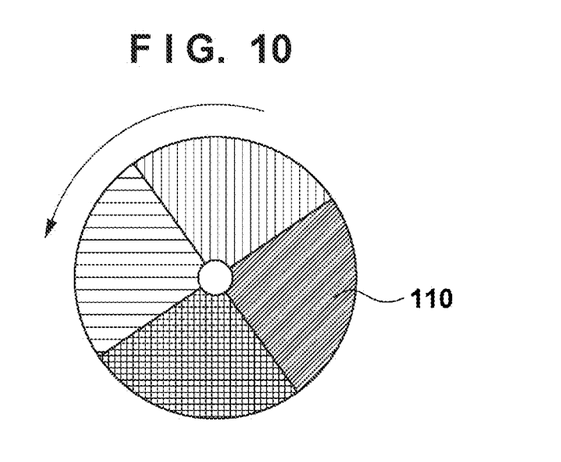
FIG. 10 is a view for exemplarily explaining an ND filter.

The reference light emerging from the fiber end of the optical fiber 102c is transmitted through an ND filter 110. The ND filter 110 is a rotatable filter for attenuating reference light. As shown in FIG. 10, the ND filter 110 is configured to change the transmittance for reference light in accordance with rotational angle, and is rotated/controlled by a light amount changing unit 115 to obtain a desired reference light amount. If the reference light amount is too large, the intensity of interfering light obtained by the interference between the reference light and return light sometimes exceeds the saturation level of each pixel of the line sensor 125 (to be described later). Since the intensity of interfering light changes depending on the amount of reference light and the amount of return light from an object to be examined (eye to be examined), it is possible to suppress the saturation of the line sensor by attenuating either or both of the reference light and the return light. In order to suppress the intensity of interfering light without losing information from the object (eye), it is preferable to attenuate only the reference light by using the ND filter 110 instead of attenuating the return light. As a means for solving this problem, the ND filter 110 may be automatically controlled to decrease the amount of reference light so as to allow the line sensor 125 to detect interfering light with a predetermined intensity. In addition, the ND filter 110 may be controlled at a time after the fiber loop 104a described above is controlled or after focus adjustment is performed (before the fiber loop 104a is controlled). Adjusting the ND filter after focus adjustment can automatically adjust the amount of light so as not to exceed a predetermined amount of light which can be applied to the object (eye).

The reference light transmitted through the ND filter 110 strikes a dispersion-compensating optical system 112 through a collimate optical system 111 and is guided to the reflecting mirror 113. The reference light reflected by the reflecting mirror 113 strikes the optical fiber 102c again through the reverse optical path. The dispersion-compensating optical system 112 corrects the dispersion of the optical system at the optical head unit 200 and an eye E to be examined. The reflecting mirror 113 is configured to be driven in the optical-axis direction by an optical-path length difference changing unit 114, and can change the optical-path length of reference light relative to the optical-path length of measurement light.

Measurement light which has entered the optical fiber 102b passes through the fiber loop 104b to change the polarization of the measurement light, and emerges from the fiber end. The polarization changing unit 105 is a control unit capable of driving each of the fiber loops 104a and 104b. Driving the fiber loop 104b will twist the optical fiber 102b and control the polarization of measurement light.

The optical head unit 200 will be described next. The optical head unit 200 is an optical block configured to be capable of moving relative to the eye E. An optical head control unit 205 is configured to be capable of driving the optical head unit 200 up and down and left and right relative to the axis of the eye E.

The light emerging from the fiber end of the optical fiber 102b is almost collimated by an optical system 202 and strikes a scanning unit 203. The scanning unit 203 is a galvano mirror capable of rotating its mirror surface, and deflects incident light. The scanning unit 203 is a two-dimensional scanning unit having two galvano mirrors, and can scan in two directions including a main scanning direction within the drawing surface and a sub-scanning direction perpendicular to the drawing surface. The light scanned by the scanning unit 203 forms an illumination spot on a retina Er of the eye E through an optical system 204. Upon undergoing in-plane deflection from the scanning unit 203, each illumination spot moves on the retina Er. Reflected light at this illumination spot position enters the optical fiber 102b through the reverse optical path and returns to the light splitting unit 103.

In the above manner, the reference light reflected by the reflecting mirror 113 and the measurement light reflected by the retina Er of the object return to the light splitting unit 103 to generate interfering light. The light generated when the reference light and the measurement light interfere with each other passes through an optical fiber 102d. The interfering light propagating to an optical system 122 is almost collimated by the optical system 122 and strikes a diffraction grating 123. The diffraction grating 123 has a periodical structure. The diffraction grating 123 spectrally separates the incident interfering light. The spectrally separated light is formed into an image on the line sensor 125 by an imaging lens 124 capable of changing the in-focus state of light. The line sensor 125 is connected to an information processing apparatus 300.

Figure 2:
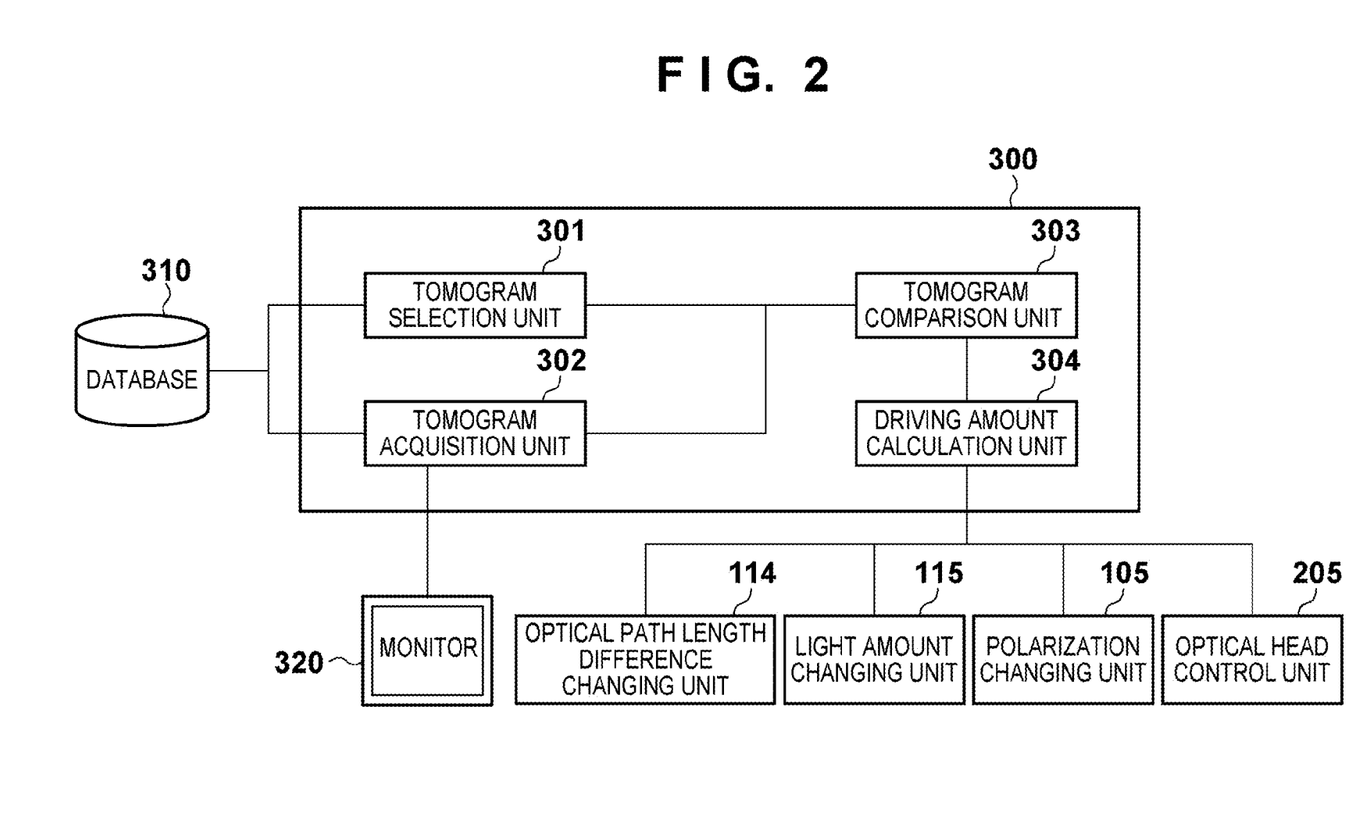
FIG. 2 is a block diagram showing the configuration of an information processing apparatus included in the optical coherence tomography apparatus.

As shown in FIG. 2, the information processing apparatus 300 included in the optical coherence tomography apparatus includes a tomogram acquisition unit 302, and acquires a tomogram of the retina by performing a Fourier transform of output data from the line sensor 125. The tomogram acquisition unit 302 is connected to a database 310 and a monitor 320 (display apparatus), and is configured to be capable of recording and displaying generated tomograms.

The information processing apparatus 300 also includes a tomogram selection unit 301, and can read out an arbitrary tomogram recorded on the database 310 in accordance with an instruction from the operator. The tomogram read out by the tomogram selection unit 301 and the tomogram acquired by the tomogram acquisition unit 302 are output to a tomogram comparison unit 303. The tomogram comparison unit 303 compares the two input tomograms, and outputs the comparison result to a driving amount calculation unit 304. The driving amount calculation unit 304 is connected to the optical path length difference changing unit 114, the light amount changing unit 115, the polarization changing unit 105, and the optical head control unit 205. The driving amount calculation unit 304 is configured to be capable of calculating a driving amount based on the comparison result obtained by the tomogram comparison unit 303 and outputting the calculated driving amount to one of the optical path length difference changing unit 114, the light amount changing unit 115, the polarization changing unit 105, and the optical head control unit 205. Based on the comparison result from the tomogram comparison unit 303, the driving amount calculation unit 304 decides which one of the members constituting the photographing optical system is to be driven to change the positional relationship between the eye and the photographing optical system including the optical path of measurement light. The driving amount calculation unit 304 outputs the calculated driving amount to a control unit which controls the operation of a driving unit for driving the decided upon member. The driving unit changes the positional relationship between the eye and the photographing optical system including the optical path of measurement light by driving the decided upon member based on the calculated driving amount. In this case, the members constituting the photographing optical system include a member for changing the optical-path length of the reference-light optical path relative to that of the measurement-light optical path and a member for changing the position of the photographing optical system relative to the eye. The members constituting the photographing optical system include a member for changing the polarization of the reference light relative to that of measurement light and a member for changing the amount of reference light relative to that of measurement light.

(Adjustment of Optical-Path Length)

An apparatus described in this embodiment is an optical coherence tomography apparatus (OCT apparatus) using a so-called Fourier domain scheme. A method of controlling the OCT apparatus of this embodiment to obtain a tomogram almost equivalent to a past tomogram will be described in detail below.

When a patient (object to be examined) who has undergone tomography by the OCT apparatus of this embodiment in the past visits the hospital again, the examiner captures a tomogram of the object under the same conditions for a past tomogram to observe the progress of an eye disease of the same object. First of all, the operator (examiner) inputs the identification information of the patient (object) by operating the operation unit. At this time, the operator may designate the type of OCT image (the macular region, optic papilla, fundus center, or the like) of a search target. The tomogram selection unit 301 searches the database 310 for a past image (tomogram) of the fundus associated with the input patient identification information. With this operation, a tomogram of the eye is found. Note that it is possible to display a list of images of the fundus of the eye and make the operator select and designate a desired image.

The examiner operates the tomogram selection unit 301 to select one of past tomograms of the patient that is to be used as a comparison source image for progress observation. The tomogram selection unit 301 reads out the selected tomogram from the database 310 and outputs it to the tomogram comparison unit 303.

The examiner operates the OCT apparatus to start capturing the current tomogram of the patient. The optical coherence information output from the line sensor 125 is input to the tomogram acquisition unit 302 of the information processing apparatus 300 and is formed into the current tomogram of the patient. The generated current tomogram of the patient is output to the tomogram comparison unit 303.

Figure 3A:
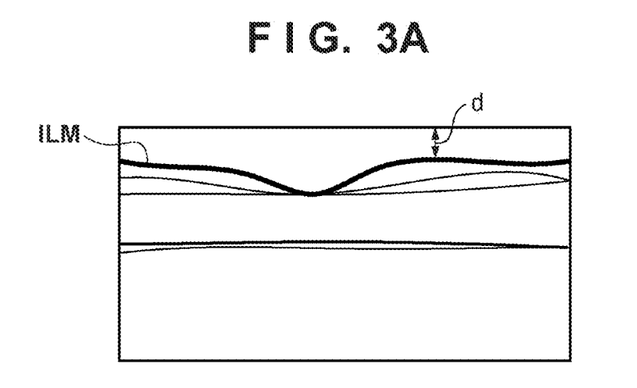
FIGS. 3A and 3B are views for explaining the detection of the position of the internal limiting membrane on tomograms.
Figure 4:
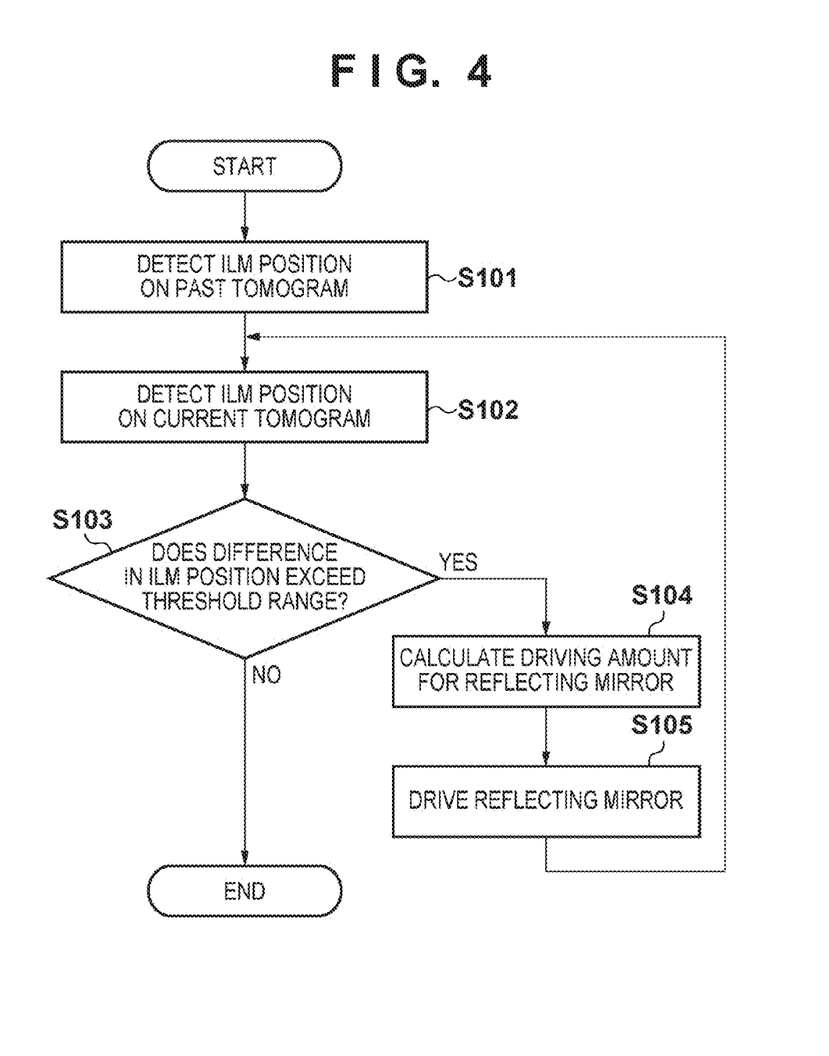
FIG. 4 is a flowchart for explaining a procedure for adjusting the optical-path length of reference light based on a difference in retinal position.

A procedure for matching the retinal position of the selected past tomogram with that of the current tomogram will be described next with reference to FIG. 4. The tomogram comparison unit 303 detects the position of the internal limiting membrane (ILM) on the tomogram indicated by "d" in FIG. 3A in the longitudinal direction in the input past tomogram (S101).

Figure 3B:
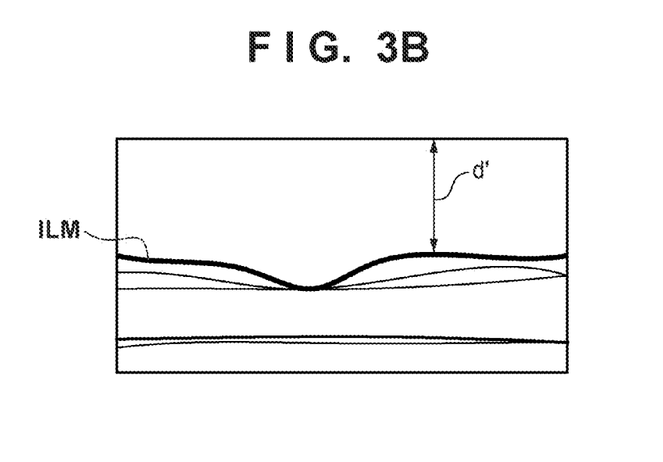

Likewise, the tomogram comparison unit 303 detects the position of the internal limiting membrane (ILM) on the tomogram indicated by "d'" in FIG. 3B in the longitudinal direction in the input current tomogram (S102). The internal limiting membrane (ILM) is located on the uppermost portion of the retina and serves as the boundary between the corpus vitreum and the retina. In general, the light reflectance of the retina is generally higher than that of the corpus vitreum, and hence the optical coherence signal intensity based on the retina is higher than that based on the corpus vitreum in the OCT apparatus. For this reason, the tomogram captured by the OCT apparatus greatly changes in luminance on the internal limiting membrane (ILM) as the boundary between the corpus vitreum and the retina. The tomogram comparison unit 303 can specify the position of the internal limiting membrane (ILM) by detecting this change in luminance information.

In this embodiment, the position (position information) of the retina is recognized by detecting the internal limiting membrane (ILM) as a constituent region of the eye in a tomogram. However, the position of the retina may be recognized by using other methods based on image information of a tomogram. For example, it is possible to specify the position of the retina by detecting the RPE layer having high luminance information instead of the internal limiting membrane (ILM).

Based on the position of the internal limiting membrane (ILM) specified in this manner, the tomogram comparison unit 303 obtains the difference between the position of the internal limiting membrane (ILM) on a past tomogram and the position of the internal limiting membrane (ILM) on a current tomogram. The tomogram comparison unit 303 determines whether the difference falls within a predetermined threshold range. Upon determining that the ILM position difference exceeds the predetermined threshold range, the tomogram comparison unit 303 outputs the ILM position difference to the driving amount calculation unit 304 (S103). The driving amount calculation unit 304 calculates a driving amount for the reflecting mirror 113 based on the input ILM position difference, and outputs the calculated driving amount to the optical path length difference changing unit 114 (S104). The optical path length difference changing unit 114 drives the reflecting mirror 113 based on the input driving amount (S105). Driving the reflecting mirror 113 will change the optical-path length of the reference-light optical path extending from the light splitting unit 103 to the reflecting mirror 113. This optical-path length then changes relative to the optical-path length of the measurement-light optical path extending from the light splitting unit 103 to the retina Er of the eye, thereby changing the optical coherence information output from the line sensor 125.

The optical coherence information newly output from the line sensor 125 is input to the tomogram acquisition unit 302 of the information processing apparatus 300 and is formed into a new current tomogram. The current tomogram acquired by newly imaging the optical coherence information is output to the tomogram comparison unit 303, which then detects the internal limiting membrane (ILM) (S102).

In step S103, the tomogram comparison unit 303 compares the positions of the internal limiting membrane (ILM). If the tomogram comparison unit 303 determines that the internal limiting membrane (ILM) position difference still exceeds the predetermined range (YES in step S103), the apparatus repeats a series of procedure in steps S104 and S105.

Upon determining in step S103 that the ILM position difference falls within the predetermined range (NO in step S103), the apparatus determines that the position of the retina in the past tomogram in the longitudinal direction almost matches that in the current tomogram, and terminates the control on the optical-path length of the reference-light optical path.

As described above, it is possible to obtain a tomogram on which the retinal position almost matches that in a past tomogram without making the operator operate the OCT apparatus according to this embodiment. In addition, this embodiment drives the reflecting mirror 113 for reference light to change the retinal position on a tomogram in the longitudinal direction. However, the embodiment may use other methods of relatively changing the optical-path lengths of a measurement-light optical path and reference-light optical path. For example, it is possible to use a method of changing the optical-path length of a measurement-light optical path by moving the optical head unit 200 or the eye to be examined or a method of changing the optical-path length of a reference-light optical path or measurement-light optical path by moving an optical member such as a prism.

(Slant Adjustment)

Figure 5A:
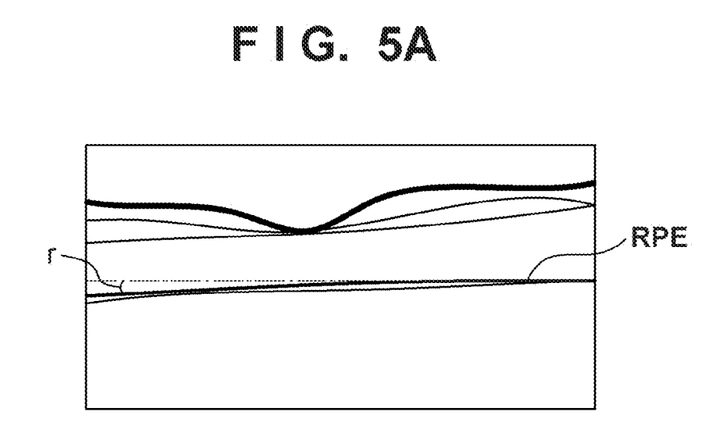
FIGS. 5A and 5B are views for explaining a difference in retinal slant due to a difference in optical head position.
Figure 6:
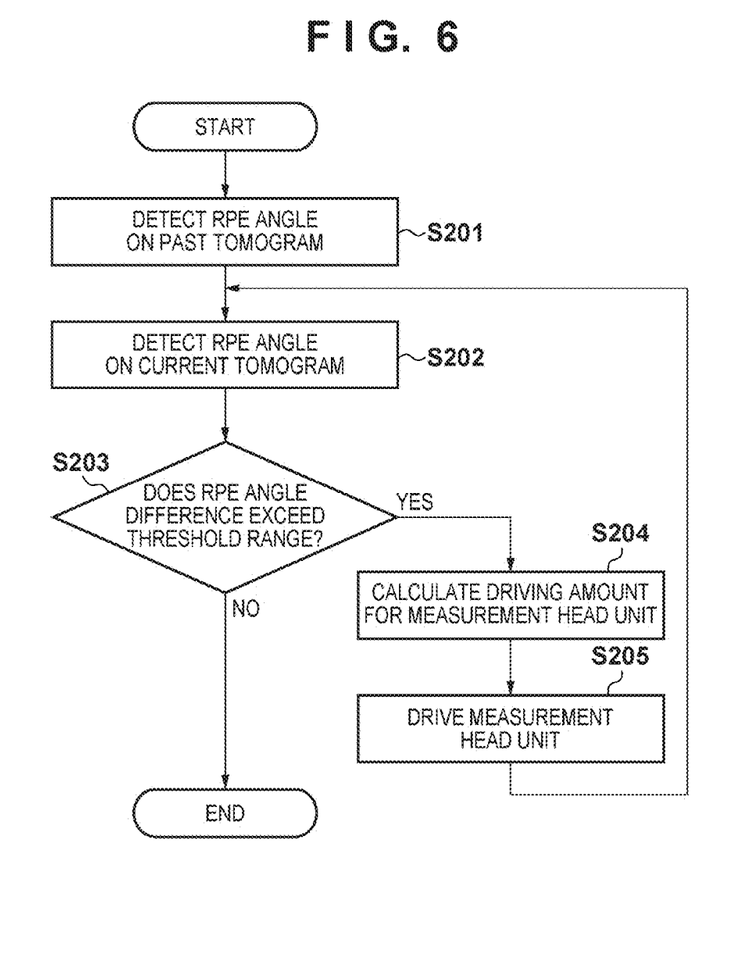
FIG. 6 is a flowchart for explaining a procedure for adjusting the optical head position based on a difference in retinal slant.

A procedure for matching the slant of the retina on a selected past tomogram with that on a current tomogram will be described next with reference to FIG. 6. The tomogram comparison unit 303 detects the angle of the retinal pigment epithelium (RPE), which is represented by r in FIG. 5A, on an input past tomogram (S201).

Figure 5B:
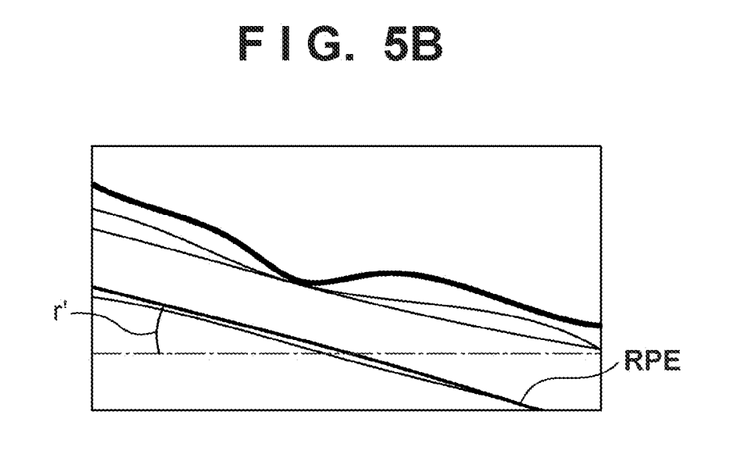

Likewise, the tomogram comparison unit 303 detects the angle of the retinal pigment epithelium (RPE), which is represented by r' in FIG. 5B, on an input current tomogram (S202). The retinal pigment epithelium (RPE) is the epithelial cell located at the boundary between the retina of the eye and choroid, and is known as a layer exhibiting the highest luminance value on the tomogram captured by the OCT apparatus. The tomogram comparison unit 303 detects the RPE layer based on this high-luminance image information, and detects the angle of the retinal pigment epithelium (RPE) by linearly approximating the detected RPE layer.

This embodiment recognizes the angle (slant information) of the retina by detecting the angle of the retinal pigment epithelium (RPE) as a constituent region of the eye on a tomogram. However, the angle of the retina may be recognized by using other methods based on the image information of a tomogram. For example, it is possible to specify the angle of the retina by detecting the internal limiting membrane (ILM) instead of the retinal pigment epithelium (RPE).

The tomogram comparison unit 303 obtains the difference between the angle of the retina on a past tomogram and that on a current tomogram based on the angle (the angle of the retina) of the retinal pigment epithelium (RPE) specified in this manner. The tomogram comparison unit 303 then determines whether the difference falls within a predetermined threshold range. Upon determining that the RPE angle difference exceeds the predetermined threshold range (YES in step S203), the tomogram comparison unit 303 outputs the RPE angle difference to the driving amount calculation unit 304 (S203). The driving amount calculation unit 304 calculates a driving amount for the optical head unit 200 based on the input RPE angle difference, and outputs the calculated driving amount to the optical head control unit 205 (S204). The optical head control unit 205 drives the optical head unit 200 based on the input driving amount (S205). Driving the optical head unit 200 will change the relative positional relationship between the eye E and the optical head unit 200. This also changes the optical coherence information output from the line sensor 125.

The tomogram acquisition unit 302 of the information processing apparatus 300 receives the optical coherence information newly output from the line sensor 125 again and forms the information into a new current tomogram. The newly captured and acquired current tomogram is output to the tomogram comparison unit 303 again to detect an RPE angle (S202).

In step S203, the apparatus compares the angles (the angles of the retina) of the retinal pigment epithelium (PRE) on the tomograms. Upon determining that the retinal pigment epithelium (PRE) angle difference still exceeds the predetermined range (YES in step S203), the apparatus repeats a series of procedure in steps S204 and S205.

Upon determining in step S203 that the retinal pigment epithelium (PRE) angle difference falls within the predetermined range (NO in step S203), the apparatus determines that the angle of the retina on the past tomogram almost matches that on the current tomogram, and terminates driving control on the optical head unit 200.

As described above, the OCT apparatus of this embodiment can obtain a tomogram on which the angle of the retina almost matches that on a past tomogram, without making the examiner perform any operation.

(Luminance Adjustment)

Figure 7A:
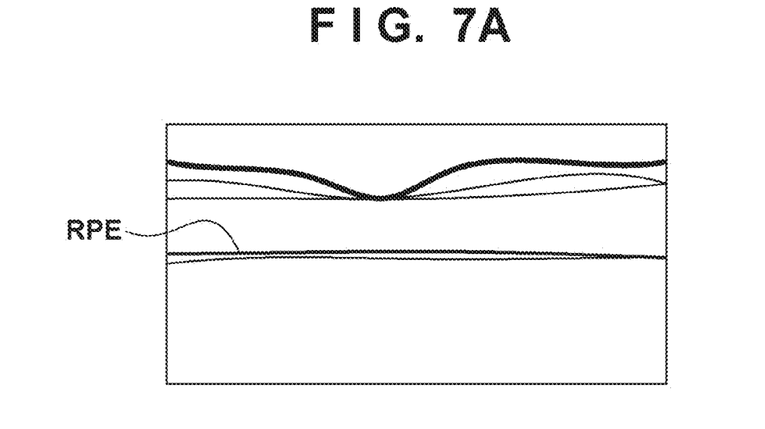
FIGS. 7A and 7B are views for explaining a difference in retinal luminance due to a difference in polarization or reference light amount.
Figure 8:
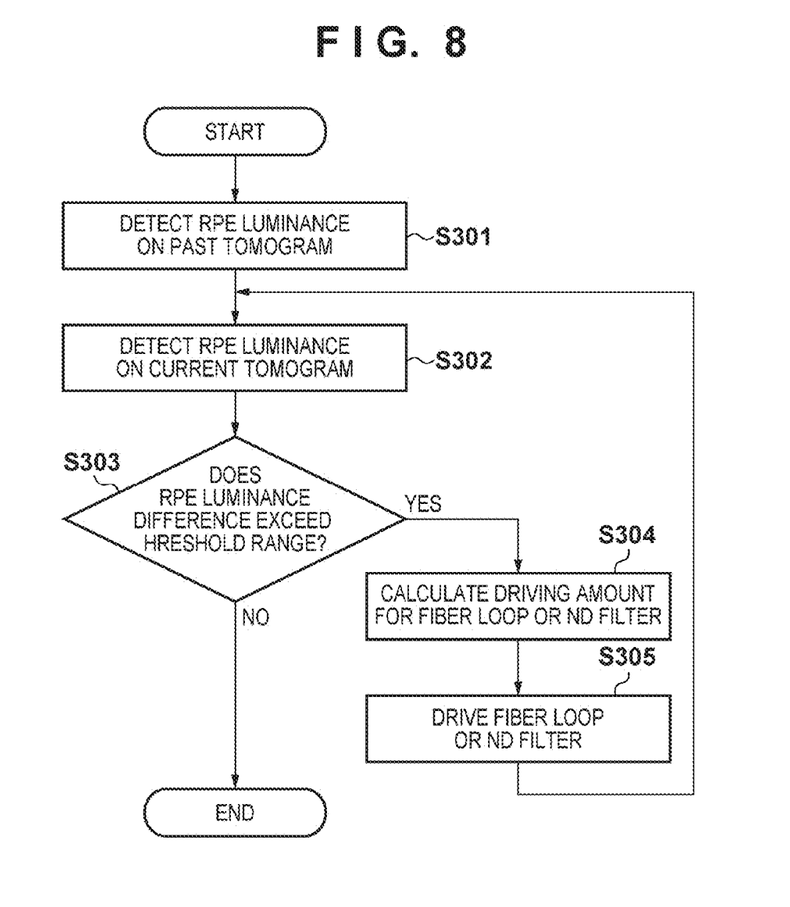
FIG. 8 is a flowchart for explaining a procedure for adjusting polarization or a reference light amount based on a difference in retinal luminance information.

A procedure for matching the brightness of the retina on a selected past tomogram with that on a current tomogram will be described next with reference to FIG. 8. The tomogram comparison unit 303 detects the luminance of the retinal pigment epithelium (PRE) on the input past tomogram shown in FIG. 7A (S301).

Figure 7B:
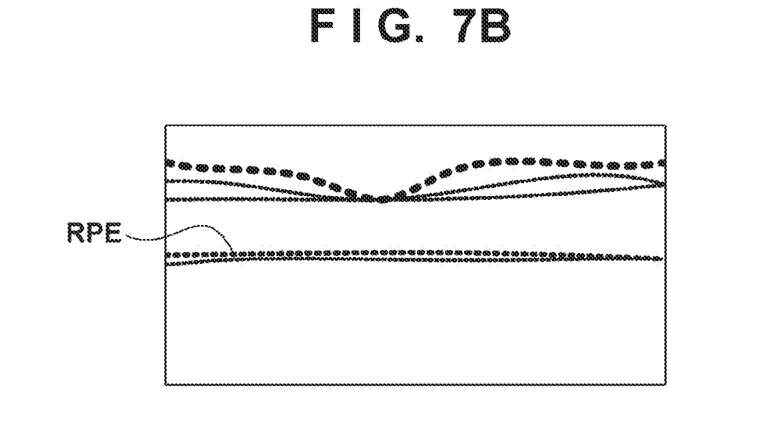

Likewise, the tomogram comparison unit 303 detects the luminance of the retinal pigment epithelium (PRE) on the input current tomogram shown in FIG. 7B (S302). The PRE layer is a layer exhibiting a high luminance value on the tomogram obtained by the OCT apparatus. In some case, however, when measurement light or reference light is not properly polarized, a clear contrast cannot be obtained. In some case, also, when the amount of reference light is not proper, the luminance of the PRE layer on a tomogram decreases. This embodiment recognizes the luminance (luminance information) of the retina by detecting the luminance of the retinal pigment epithelium (PRE) as a constituent region of the eye to be examined on a tomogram. However, the luminance of the retina may be recognized by using other methods based on the image information of a tomogram. For example, it is possible to specify the luminance of the retina by detecting the internal limiting membrane (ILM) instead of the retinal pigment epithelium (RPE).

The tomogram comparison unit 303 obtains the difference between the luminance of the retina on a past tomogram and that on a current tomogram based on the luminance (the luminance of the retina) of the retinal pigment epithelium (RPE) specified in this manner. The tomogram comparison unit 303 then determines whether the difference falls within a predetermined threshold range. The tomogram comparison unit 303 outputs the RPE luminance difference to the driving amount calculation unit 304 (S303) upon determining that the RPE luminance difference exceeds the predetermined threshold range (YES in step S303). The driving amount calculation unit 304 calculates a driving amount for at least one of the fiber loops 104a and 104b based on the input RPE luminance difference, and outputs the calculated driving amount to the polarization changing unit 105 (S304). The polarization changing unit 105 drives the fiber loop 104 (at least one of the fiber loops 104a and 104b) based on the input driving amount (S305), as shown in, for example, FIG. 9. Driving at least one of the fiber loops 104a and 104b will relatively change the polarization of the measurement-light optical path and that of the reference-light optical path. This also changes the optical coherence information output from the line sensor 125.

The tomogram acquisition unit 302 of the information processing apparatus 300 receives the optical coherence information newly output from the line sensor 125 again and forms the information into a new current tomogram. The newly captured and acquired current tomogram is output to the tomogram comparison unit 303 again to detect a RPE luminance (S302).

In step S303, the apparatus compares the luminances (the luminances of the retina) of the retinal pigment epithelium (PRE) on the tomograms. Upon determining that the retinal pigment epithelium (PRE) luminance difference still exceeds the predetermined range (YES in step S303), the apparatus repeats the series of procedures in steps S304 and S305.

Upon determining in step S303 that the retinal pigment epithelium (PRE) luminance difference falls within the predetermined range (NO in step S303), the apparatus determines that the luminance of the retina on the past tomogram almost matches that on the current tomogram, and terminates driving control on the fiber loop 104.

As described above, the OCT apparatus of this embodiment can obtain a tomogram on which the luminance of the retina almost matches that on a past tomogram, without making the examiner perform any operation.

(Adjustment of Light Amount)

This embodiment changes the luminance of the retina on a tomogram by driving at least one of the fiber loops 104a and 104b. In another form, it is possible to change the luminance of the retina by changing the amount of reference light. For example, the rotatable ND filter 110 having a density gradient like that shown in FIG. 10 is placed in the reference-light optical path to make the driving amount calculation unit 304 calculate the rotational angle of the ND filter 110 based on an input RPE luminance difference (S304). The calculated rotational angle is output to the light amount changing unit 115, which then drives the ND filter 110 (S305).

With the above procedure, it is possible to obtain a tomogram whose retinal luminance almost matches that of a past tomogram. This embodiment allows the apparatus to easily capture tomograms suitable for progress observation. For example, it is possible to achieve matching not only in position in the X and Y directions between tomograms to be compared, but also to achieve matching of the coherence gate (a position corresponding to a reference optical-path length in a measurement optical path), the slant, the brightness, and the like. This makes it possible to easily capture tomograms suitable for progress observation.

The ophthalmic system according to the embodiment of the present invention includes the above optical coherence tomography apparatus and a storage apparatus. The storage apparatus can store the first tomogram of a predetermined region of the fundus of the eye to be examined. The optical coherence tomography apparatus can acquire the second tomogram of a predetermined region of the fundus of the eye to be examined, based on the interfering light obtained by the interference between return light from the eye irradiated with measurement light through the scanning unit and reference light corresponding to the measurement light.

The optical coherence tomography apparatus includes a driving unit which drives a member of the optical coherence tomography apparatus and a control unit which controls a driving unit so as to make the difference in image information between the first and second tomograms fall within a predetermined range. The control unit changes the position of the coherence gate by driving the driving unit so as to make the difference between the position of a predetermined layer on the first tomogram and that on the second tomogram fall within a predetermined range. When the control unit controls the driving of the driving unit, the optical coherence tomography apparatus acquires the third tomogram of a predetermined region of the fundus of the eye to be examined. The optical coherence tomography apparatus includes a photographing optical system which splits light from a light source into measurement light and reference light, irradiates the eye to be examined with the measurement light through the measurement-light optical path, guides the reference light to the reference-light optical path, and outputs interfering light obtained by the interference between the reference light and return light from the eye. In this case, the members constituting the photographing optical system include a member for changing the optical-path length of the reference-light optical path relative to the optical-path length of the measurement-light optical path and a member for changing the position of the photographing optical system relative to the eye to be examined. Alternatively, the members constituting the photographing optical system include a member for changing the polarization of reference light relative to that of measurement light and a member for changing the amount of reference light relative to that of measurement light.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer, for example, via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-079802, filed Mar. 31, 2011, which is hereby incorporated by reference herein in its entirety.

What is claimed is:

1. An optical coherence tomography apparatus comprising:
   an acquisition unit configured to split light from a light source into measurement light and reference light, irradiate an eye to be examined with the measurement light through a measurement light optical path, guide the reference light to a reference light optical path, and acquire a tomographic image of the eye based on interfering light obtained by interference between the reference light and return light from the eye;
   a positional relationship changing unit configured to change a positional relationship between the eye and an optical system including an optical path of the measurement light;
   a readout unit configured to read out from a database a tomographic image of a region including the same region of the eye as the region of the eye in the acquired tomographic image; and
   a control unit configured to control said positional relationship changing unit based on a difference in slant information of the eye between the acquired tomographic image and the read out tomographic image.

2. The apparatus according to claim 1, wherein said control unit controls said positional relationship changing unit so as to make the difference in the slant information fall within a predetermined range.

3. The apparatus according to claim 1, further comprising an optical path length difference changing unit configured to change a difference between an optical path length of the measurement light optical path and an optical path length of the reference light optical path,
   wherein said control unit controls said optical path length difference changing unit based on a difference in position information of a predetermined region of the eye between the acquired tomographic image and the read out tomographic image.

4. The apparatus according to claim 1, further comprising a polarization changing unit configured to change the polarization of the reference light relative to polarization of the measurement light,
   wherein said control unit controls said polarization changing unit based on a difference in luminance information of a predetermined region of the eye between the acquired tomographic image and the read out tomographic image.

5. The apparatus according to claim 1, further comprising a light amount changing unit configured to change a light amount of the reference light relative to a light amount of the measurement light,
   wherein said control unit controls said light amount changing unit based on a difference in luminance information of a predetermined region of the eye between the acquired tomographic mage and the read out tomographic image.

6. The apparatus according to claim 1, further comprising:
   an input unit configured to input identification information of the eye to be examined,
   wherein said read out unit reads out from the database the tomographic image of the region including the same region based on the input identification information.

7. The apparatus according to claim 1, further comprising:
   a comparison unit configured to compare the read out tomographic image with the acquired tomographic image;
   a detection unit configured to detect an angle of a predetermined layer in the acquired tomographic image relative to a predetermined layer in the read out tomographic image based on a comparison result of said comparison unit; and
   a calculation unit configured to calculate an amount for changing the positional relationship based on the detected angle,
   wherein said control unit controls said positional relationship changing unit based on the amount calculated as the difference in the slant information.

8. The apparatus according to claim 1, wherein said positional relationship changing unit changes the positional relationship by moving the optical system relative to the eye.

9. An ophthalmic system comprising:
   a storage apparatus configured to store a first tomographic image of a predetermined region of a fundus of an eye to examined;
   an optical coherence tomography apparatus configured to acquire a second tomographic image of the predetermined region of the fundus of the eye based on interfering light obtained by interference between return light from the eye irradiated with measurement light and reference light corresponding to the measurement light; and
   a readout apparatus configured to read out from said storage apparatus the first tomographic image of a region including the same region of the eye as the region of the eye in the acquired second tomographic image,
   wherein said optical coherence tomography apparatus comprises
   (a) a driving unit configured to drive a member of said optical coherence tomography apparatus, and
   (b) a control unit configured to control said driving unit so as to make a difference in at least one of slant information of the eye and luminance information of a predetermined region of the eye between the first tomographic image and the second tomographic image fall within a predetermined range.

10. The system according to claim 9, wherein when driving of said driving unit is controlled by said control unit, said optical coherence tomography apparatus acquires a third tomographic image of the predetermined region of the fundus of the eye.

11. The system according to claim 9, wherein said control unit changes a position of a coherence gate by driving said driving unit so as to make a difference in a position of a predetermined layer between the first tomographic image and the second tomographic image fall within a predetermined range.

12. A method of controlling an optical coherence tomography apparatus, the method comprising:
   an acquisition step of splitting light from a light source into measurement light and reference light, irradiating an eye to be examined with the measurement light through a measurement light optical path, guiding the reference light to a reference light optical path, and acquiring a tomographic image of the eye based on interfering light obtained by interference between the reference light and return light from the eye;

a readout step of reading out from a database a tomographic image of a region including the same region of the eye as the region of the eye in the acquired tomographic image; and a control step of controlling, based on a difference in slant information of the eye between the acquired tomographic image and the read out tomographic image, a positional relationship changing unit which is configured to change a positional relationship between the eye and an optical system including an optical path of the measurement light.

13. A non-transitory computer-readable storage medium storing a program which causes a computer to execute each step of a method, according to claim 12, of controlling an optical coherence tomography apparatus.

14. The method according to claim 12, wherein the change in positional relationship is such so as to make the difference in the slant information fall within a predetermined range.

15. The method according to claim 12, further comprising a step of controlling, based on a difference in position information of a predetermined region of the eye between the acquired tomographic image and the read out tomographic image, an optical path length difference changing unit which is configured to change a difference between an optical path length of the measurement light optical path and an optical path length of the reference light optical path.

16. The method according to claim 12, further comprising a step of controlling, based on a difference in luminance information of a predetermined region of the eye between the acquired tomographic image and the read out tomographic image, a polarization changing unit which is configured to change the polarization of the reference light relative to polarization of the measurement light.

17. The method according to claim 12, further comprising a step of controlling, based on a difference in luminance information of a predetermined region of the eye between the acquired tomographic image and the read out tomographic image, a light amount changing unit which is configured to change a light amount of the reference light relative to a light amount of the measurement light.

18. The method according to claim 12, further comprising:
an input step of inputting identification information of the eye to be examined,
wherein in the readout step, the tomographic image of the region including the same region is read out from the database based on the input identification information.

19. The method according to claim 12, further comprising:
a comparison step of comparing the read out tomographic image with the acquired tomographic image;
a detection step of detecting an angle of a predetermined layer in the acquired tomographic image relative to a predetermined layer in the read out tomographic image based on a comparison result in the comparison step; and
a calculation step of calculating an amount for changing the positional relationship based on the detected angle,
wherein in the control unit step, the positional relationship changing unit is controlled based on the amount calculated as the difference in the slant information.

20. An ophthalmic system comprising:
an acquisition unit configured to split light from a light source into measurement light and reference light, irradiate an eye to be examined with the measurement light through a measurement light optical path, guide the reference light to a reference light optical path, and acquire a tomographic image of the eye based on interfering light obtained by interference between the reference light and return light from the eye;

a positional relationship changing unit configured to change a positional relationship between the eye and an optical system including an optical path of the measurement light;

a readout unit configured to read out from a database a tomographic image of a region including the same region of the eye as the region of the eye in the acquired tomographic image; and a control unit configured to control said positional relationship changing unit based on a difference in slant information of the eye between the acquired tomographic image and the read out tomographic image.

21. The ophthalmic system according to claim 20, wherein said control unit controls said positional relationship changing unit so as to make the difference in the slant information fall within a predetermined range.

22. The ophthalmic system according to claim 20, further comprising an optical path length difference changing unit configured to change a difference between an optical path length of the measurement light optical path and an optical path length of the reference light optical path, and
wherein said control unit controls said optical path length difference changing unit based on a difference in position information of a predetermined region of the eye between the acquired tomographic image and the read out tomographic image.

23. The ophthalmic system according to claim 20, further comprising a polarization changing unit configured to change the polarization of the reference light relative to polarization of the measurement light, and
wherein said control unit controls said polarization changing unit based on a difference in luminance information of a predetermined region of the eye between the acquired tomographic image and the read out tomographic image.

24. The ophthalmic system according to claim 20, further comprising a light amount changing unit configured to change a light amount of the reference light relative to a light amount of the measurement light, and
wherein said control unit controls said light amount changing unit based on a difference in luminance information of a predetermined region of the eye between the acquired tomographic image and the read out tomographic image.

25. The ophthalmic system according to claim 20, further comprising:
an input unit configured to input identification information of the eye to be examined,
wherein said readout unit reads out from the database the tomographic image of the region including the same region based on the input identification information.

26. A non-transitory computer-readable storage medium storing a program which causes a computer to function as each unit of an optical coherence tomography apparatus of an ophthalmic system defined in claim 20.

27. An optical coherence tomography apparatus comprising:
an acquisition unit configured to split light from a light source into measurement light and reference light, irradiate an eye to be examined with the measurement light through a measurement light optical path, guide the reference light to a reference light optical path, and acquire a tomographic image of the eye based on interfering light obtained by interference between the reference light and return light from the eye;

a polarization changing unit configured to change the polarization of the reference light relative to polarization of the measurement light;

a readout unit configured to read out from a database a tomographic image of a region including the same region of the eye as the region of the eye in the acquired tomographic image; and a control unit configured to control said polarization changing unit based on a difference in luminance information of a predetermined region of the eye between the acquired tomographic image and the read out tomographic image.

28. A method of controlling an optical coherence tomography apparatus, the method comprising:

an acquisition step of splitting light from a light source into measurement light and reference light, irradiating an eye to be examined with the measurement light through a measurement light optical path, guiding the reference light to a reference light optical path, and acquiring a tomographic image of the eye based on interfering light obtained by interference between the reference light and return light from the eye;

a readout step of reading out from a database a tomographic image of a region including the same region of the eye as the region of the eye in the acquired tomographic image; and a control step of controlling, based on a difference in luminance information of a predetermined region of the eye between the acquired tomographic image and the read out tomographic image, a polarization changing unit which is configured to change the polarization of the reference light relative to polarization of the measurement light.

29. A non-transitory computer-readable storage medium storing a program which causes a computer to execute each step of a method, according to claim 28, of controlling an optical coherence tomography apparatus.

30. An optical coherence tomography apparatus comprising:

an acquisition unit configured to split light from a light source into measurement light and reference light, irradiate an eye to be examined with the measurement light through a measurement light optical path, guide the reference light to a reference light optical path, and acquire a tomographic image of the eye based on interfering light obtained by interference between the reference light and return light from the eye;

a light amount changing unit configured to change a light amount of the reference light relative to a light amount of the measurement light;

a read out unit configured to read out from a database a tomographic image of a region including the same region of the eye as the region of the eye in the acquired tomographic image; and a control unit configured to control said light amount changing unit based on a difference in luminance information of a predetermined region of the eye between the acquired tomographic image and the read out tomographic image.

31. A method of controlling an optical coherence tomography apparatus, the method comprising:

an acquisition step of splitting light from a light source into measurement light and reference light, irradiating an eye to be examined with the measurement light through a measurement light optical path, guiding the reference light to a reference light optical path, and acquiring a tomographic image of the eye based on interfering light obtained by interference between the reference light and return light from the eye;

a readout step of reading out from a database a tomographic image of a region including the same region of the eye as the region of the eye in the acquired tomographic image; and a control step of controlling, based on a difference in luminance information of a predetermined region of the eye between the acquired tomographic image and the read out tomographic image, a light amount changing unit which is configured to change a light amount of the reference light relative to a light amount of the measurement light.

32. A non-transitory computer-readable storage medium storing a program which causes a computer to execute each step of a method, according to claim 31, of controlling an optical coherence tomography apparatus.

* * * * *